(12) United States Patent
Tomala et al.

(10) Patent No.: US 10,691,776 B1
(45) Date of Patent: Jun. 23, 2020

(54) METHODS AND SYSTEMS FOR PREDICTING ADHERENCE TO MULTIPLE SCLEROSIS TREATMENT

(71) Applicant: Express Scripts, Inc., St. Louis, MO (US)

(72) Inventors: David Alfredo Tomala, Chesterfield, MO (US); Seda Aydin Follis, St. Louis, MO (US); Suman Katragadda, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 359 days.

(21) Appl. No.: 13/969,707

(22) Filed: Aug. 19, 2013

Related U.S. Application Data

(60) Provisional application No. 61/684,307, filed on Aug. 17, 2012.

(51) Int. Cl.
*G16H 10/20* (2018.01)
*G06F 19/00* (2018.01)

(52) U.S. Cl.
CPC ............... *G06F 19/3456* (2013.01)

(58) Field of Classification Search
CPC .................................. G06F 19/3456
See application file for complete search history.

(56) References Cited

U.S. PATENT DOCUMENTS

2008/0126130 A1* 5/2008 Miller ............... G06Q 50/24
705/3

OTHER PUBLICATIONS

Kripalani, Sunil, Jessica Risser, Margaret Gatti and Terry A. Jacobson. Development and Evaluation of the Adherence to Refills and Medications Scale (ARMS) among Low-Literacy Patients with Chronic Disease. International Society for Pharmacoeconomics and Outcomes Research, 2008. pp. 118-123.*
Harrell, Jr., Frank E. Regression Modeling Strategies. Springer Science + Business Media, New York, 2001.*

* cited by examiner

*Primary Examiner* — Linh Giang Le
(74) *Attorney, Agent, or Firm* — Husch Blackwell LLP

(57) ABSTRACT

Methods and systems for predicting adherence to Multiple Sclerosis treatment are described. In one embodiment, a member undergoing a Multiple Sclerosis treatment is identified. Member data associated with the member undergoing the Multiple Sclerosis treatment is accessed. Pre-prediction time period adherence data associated with the member, member prescription data associated with the member, member family data associated with the member, and member demographic data associated with the member are determined based on the member data associated with the member. A likelihood that the member will be adherent to the Multiple Sclerosis treatment over a prediction time period is determined based on the pre-prediction time period adherence data, member prescription data, member family data, and member demographic data. Other methods and systems are described.

10 Claims, 7 Drawing Sheets

METHODS AND SYSTEMS FOR PREDICTING ADHERENCE TO MULTIPLE SCLEROSIS TREATMENT

CROSS-REFERENCE TO A RELATED APPLICATION

This application claims the benefit of U.S. Provisional Patent Application 61/684,307, filed on 17 Aug. 2012, entitled "Methods and Systems for Predicting Adherence to Multiple Sclerosis Treatment," the entire disclosure of which is incorporated herein by reference.

FIELD

The field relates to predictive modeling for treatment adherence, and more particularly to predictive modeling for predicting adherence to Multiple Sclerosis treatment.

BACKGROUND

For patients with Multiple Sclerosis, adherence to disease modifying therapy can often be important for altering the clinical progression of the disease, to thereby prevent, or reduce, the occurrences of costly hospitalizations. Metrics for determining adherence, such as medication possession ratio, are commonly used for gauging a patient's adherence to a treatment regimen or protocol. Such metrics can often present an incomplete, or less than accurate, understanding of a patient's adherence to the treatment regimen or protocol, and may not serve as an accurate basis for predicting future adherence to the treatment regimen or protocol.

DETAILED DESCRIPTION

Figure 1:
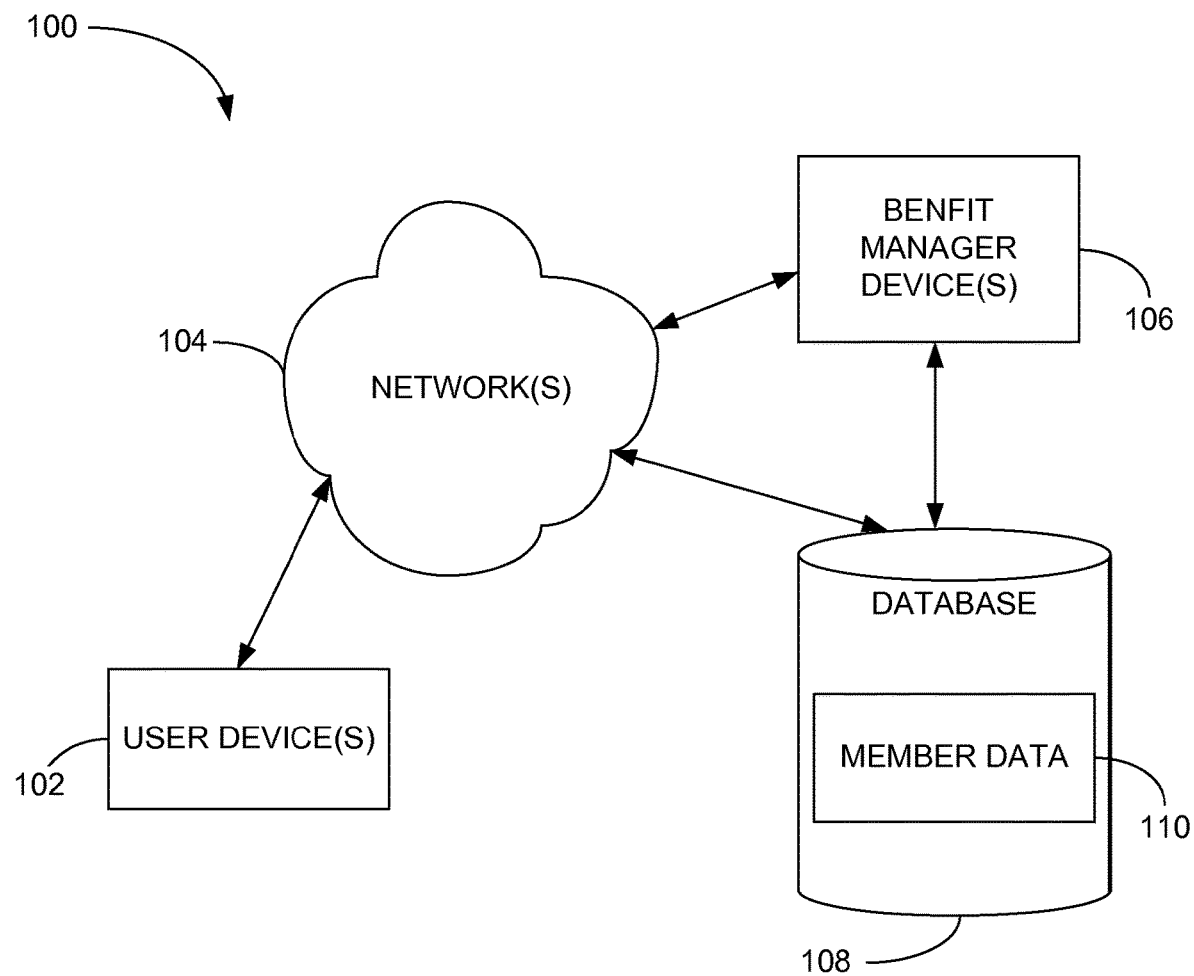
FIG. 1 is a block diagram of an example system, according to an example embodiment.

Example methods and systems for predicting adherence to Multiple Sclerosis treatment are described. In the following description, for purposes of explanation, numerous specific details are set forth in order to provide a thorough understanding of example embodiments. It will be evident, however, to one of ordinary skill in the art that embodiments of the invention may be practiced without these specific details. Further, while example methods and systems for predicting adherence to Multiple Sclerosis treatment as described, it will be appreciated that the methods and systems described herein may be applicable to predicting adherence to treatments for other conditions and/or diseases.

In general, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company in which the PBM services are offered directly by the health insurance company or offered indirectly by the PBM on behalf of the health insurance company.

The client may utilize the services of the PBM monitor and/or encourage adherence of members to treatment regimens or protocols. Improved adherence to treatments, for example of chronic conditions such as Multiple Sclerosis, may reduce and/or delay the occurrence of costly hospitalizations of members, and thereby reducing the costs of health plans offered by the client to members. In order to provide effective allocation of resources toward improving member adherence to treatment, the PBM may utilize predictive adherence models, which may provide an indication of whether a given member is likely to be adherent in the future to the treatment or whether the member is likely to be non-adherent to the treatment. Benefits may be realized by allocating resources to monitoring, encouraging, and/or intervening in the treatment adherence of members who are likely to be non-adherent, as compared to allocating resources to members who are likely to be adherent regardless of any monitoring, encouraging, or intervening in their treatment by the PBM. In some embodiments, intervening at the start of therapy may be two to four times more effective than waiting 180 days. In some embodiments, the early prediction may enable an early intervention, which then provides the member (and the client) of the benefit from the enhanced effectiveness of early interventions.

FIG. 1 is a block diagram of an example system 100, according to an example embodiment. The system 100 is an example embodiment in which a likelihood of member adherence to a Multiple Sclerosis treatment may be predicted. The system 100 includes a user device 102 in communication with a benefit manager device 106 over a network 104.

The user device 102 is used by a device operator. The user device 102 may be a stand-alone device that solely provides at least some of the functionality to enable the prediction of adherence to Multiple Sclerosis treatment, or may be a multi-use device that has functionality outside of predicting adherence to Multiple Sclerosis treatment as described herein. Examples of the user device 102 include a set-top box (STB), a receiver card, a mobile telephone, a personal digital assistant (PDA), a display device, a portable gaming unit, and a computing system; however other devices may also be used. In some embodiments, the computing system. For example, the user device 102 may include a mobile electronic device, such an IPHONE or IPAD device by Apple, Inc., mobile electronic devices powered by ANDROID by Google, Inc., and a BLACKBERRY device by Research In Motion Limited. The user device 102 also include other computing devices, such as desktop computing devices, notebook computing devices, netbook computing devices, gaming devices, and the like. Other types of electronic devices may also be used.

The network 104 by which the user device 102 communicates with the benefit manager device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The user device 102 may be in a client-server relationship with the benefit manager device 106, a peer-to-peer relationship with the benefit manager device 106, and/or in a different type of relationship with the benefit manager device 106.

The benefit manager device 106 may be in communication directly (e.g., through local storage) and/or through the network 104 (e.g., in a cloud configuration or software as a service) with a database 108. The database 108 may be deployed on the user device 102, the benefit manager device 106, both the user device 102 and the benefit manager device 106, partially on the user device 102 and partially on the benefit manager device 106, on a separate device, or may otherwise be deployed. The database 108 may store member data 110.

The member data 110 includes information regarding members of drug benefit plans managed by the PBM. In general, the member data 110 may include information about the member (e.g., member identity, member gender, member date of birth, member demographic and economic data, member family data, and the like), information about medications taken by the member (e.g., prescriptions filled by the member, fill dates associated with prescriptions filled by the member, quantities of drugs in prescriptions filled by the member, prescription claims adjudication data, and the like). The member data 110 may include additional information about the members. While the member data 110 is shown residing in a single database, it will be appreciated that the member data 110 may reside in one, or more than one, databases. In some embodiments, the various aspects of the member data 110 may be stored in separate databases. For example, in some embodiments, member data including member prescription data may be stored in a first database, and member demographic data may be stored in a second database. In some embodiments, all member data may be stored in a single database.

While the system 100 in FIG. 1 is shown to include single devices 102, 106, multiple devices may be used. The devices 102, 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106 or in parallel to link the devices 102, 106.

Figure 2:
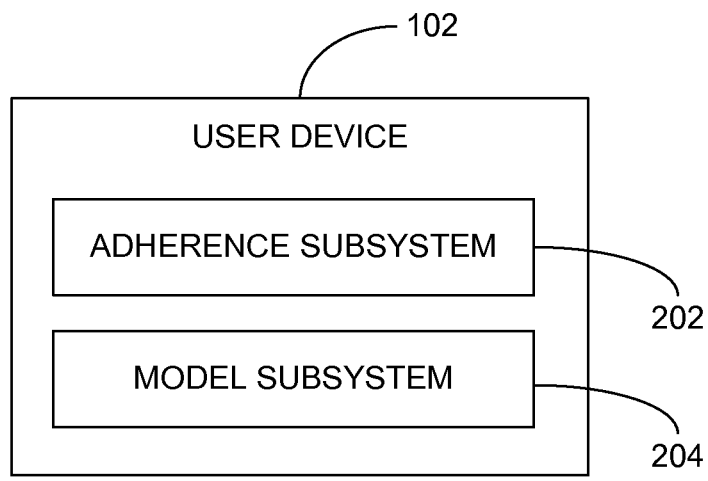
FIG. 2 is a block diagram of an example user device that may be deployed within the system of FIG. 1, according to an example embodiment.

FIG. 2 illustrates the user device 102, according to an example embodiment. The user device 102 may be used by a device operator to predict likelihood of member adherence to a Multiple Sclerosis treatment over a prediction time period. The user device 102 may be deployed in the system 100, or may otherwise be used.

The user device 102 may include an adherence subsystem 202 and a model subsystem 204. In some embodiments, the adherence subsystem 202 may enable a likelihood of member adherence to a Multiple Sclerosis treatment over a prediction time period to be determined. For example, the adherence subsystem 202 may enable a likelihood of a member being adherent to the Multiple Sclerosis treatment over the next six months to be determined. Other prediction time periods may be utilized, for example a three month prediction time period, a one year prediction time period, or other suitable time period. In some embodiments, the model subsystem 204 may enable a Multiple Sclerosis adherence predictive model to be generated. The generated Multiple Sclerosis adherence predictive model may enable a likelihood of member adherence to a Multiple Sclerosis treatment to be determined.

In some embodiments, the time period for which prediction may occur may be a rolling period in which a prediction is made for a certain period of time. In some embodiments, the time period for which prediction may occur may be a fixed period of time (e.g., a calendar year). In embodiments where there is a fixed period of time, a mathematical minimum and mathematical maximum (e.g., based on prescription drug fills made or missed) may be used in combination of the adherence model (e.g., as the time period progress) to make predictions and/or to make targeting/intervention decisions.

Figure 3:
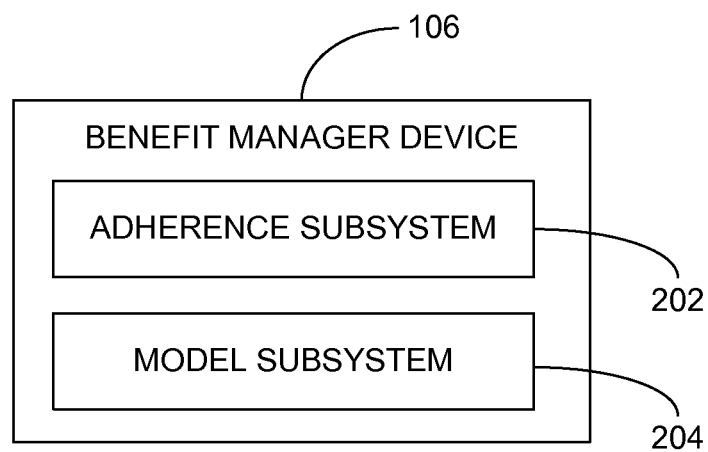
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the adherence subsystem 202. In some embodiments, the adherence subsystem 202 when used may provide server-side functionality to the user device 102. By way of example, the adherence subsystem 202 may be deployed in both the user device 102 and the benefit manager device 106. The user device 102 may then perform some of the functionality while other functionality is performed by the benefit manager device 106.

In some embodiments, the benefit manager device 106 may include the model subsystem 204. In some embodiments, the model subsystem 204 when used may provide server-side functionality to the user device 102. By way of example the model subsystem 204 may be deployed in both the user device 102 and the benefit manager device 106. The user device may then perform some of the functionality while other functionality is performed by the benefit manager device 106.

Figure 4:
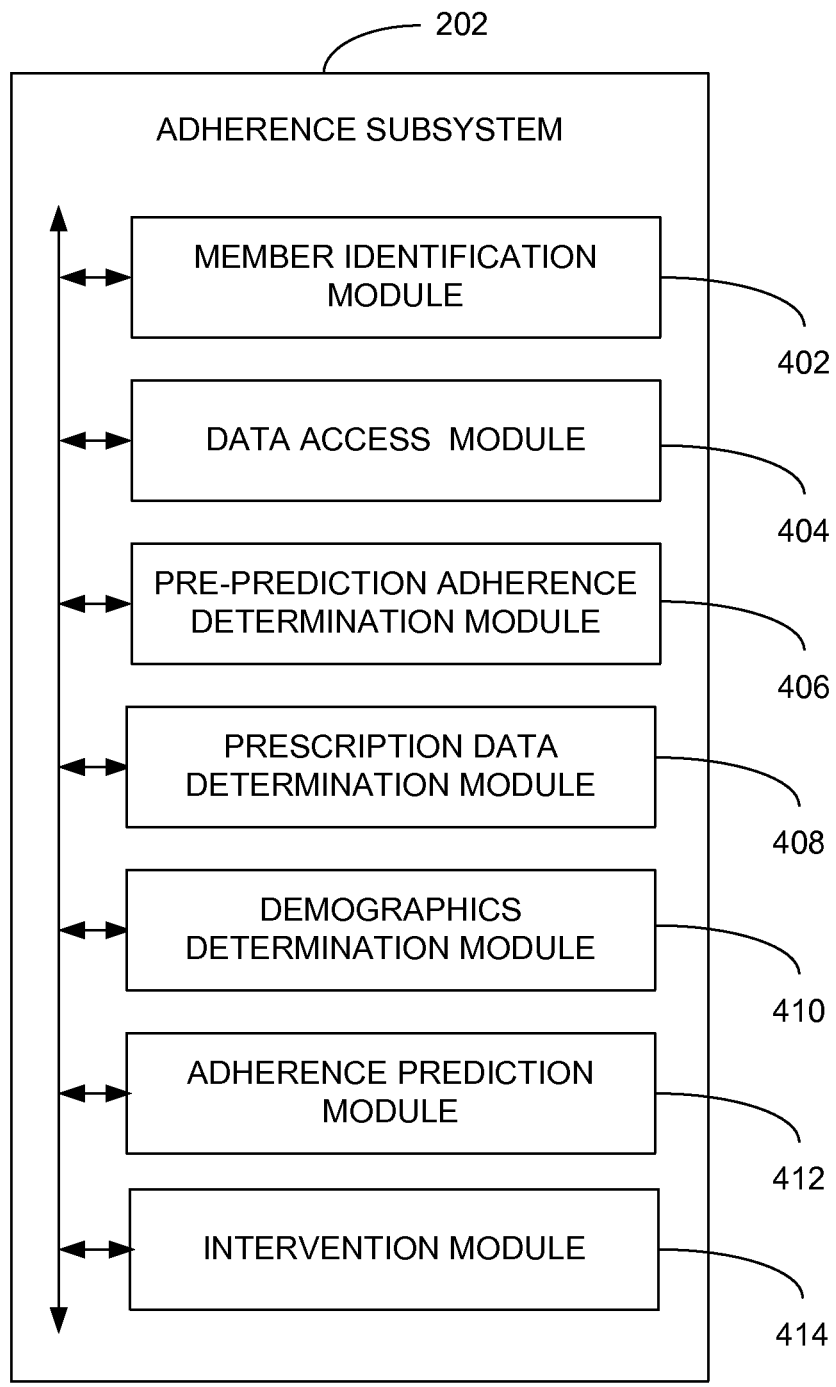
FIG. 4 is a block diagram of an example adherence subsystem that may be deployed within the user device of FIG. 2 or the benefit manager device of FIG. 3, according to an example embodiment.

FIG. 4 illustrates an example of the adherence subsystem 202 that may be deployed in the user device 102, the benefit manager device 106, or otherwise deployed in another system. One or more modules are communicatively coupled and included in the adherence subsystem 202 to enable the determination of a likelihood that a member will be adherent to a Multiple Sclerosis treatment over a prediction time period. The modules of the adherence subsystem 202 that may be included are a member identification module 402, a data access module 404, a pre-prediction adherence determination module 406, a prescription data determination module 408, a demographics determination module 410, an adherence prediction module 412, and an intervention module 414.

In some embodiments, the modules of the adherence subsystem 202 may be distributed so that some of the modules are deployed in the user device 102 and some modules are deployed in the benefit manager device 106. In one embodiment, the modules are deployed in memory and executed by a processor coupled to the memory. The functionality contained within the modules 402-414 may be combined into a lesser number of modules, further divided among a greater number of modules, or redistributed among existing modules. Other configurations including the functionality of the modules 402-414 may be used.

In some embodiments, the member identification module 402 may identify a member, or more than one member, undergoing a Multiple Sclerosis treatment. The member may be identified as undergoing a Multiple Sclerosis treatment based on a determination that the member has filled a prescription for a Multiple Sclerosis drug and/or based on analysis of data reflecting that the member has been enrolled in a Multiple Sclerosis therapy program offered by the PBM or by another entity. Claims for prescriptions for Multiple Sclerosis drugs and/or Multiple Sclerosis therapy program may be adjudicated by the PBM, thereby enabling the member identification module 402 to identify the member as undergoing the Multiple Sclerosis treatment (e.g., based on claim data). For example, the member identification module 402 may identify a member undergoing the Multiple Sclerosis treatment when a pharmacy claim for a Multiple Sclerosis drug is received from a pharmacy. In an embodiment, the member identification module 402 may execute a query over claim data to identify members who have filled a prescription for a Multiple Sclerosis drug and had their pharmacy claims adjudicated.

In some embodiments, the data access module 404 may access member data 110 from the database 108. In some embodiments, the data access module 404 may access the member data by receiving the member data 110. Receiving the member data 110 may include, for example, receiving the member data through the network 104 from the user device 102, from the benefit manager device 106, or from a different device.

In some embodiments, the pre-prediction adherence determination module 406 may determine pre-prediction adherence data associated with the member based on the member data 110 accessed by the data access module 404. For example, the adherence determination module 406 may generally determine adherence of the member to a Multiple Sclerosis drug associated with the Multiple Sclerosis treatment for a time period that is prior to the time period for which a likelihood of adherence is being determined by the adherence subsystem 202. By way of example, member data for a six-month period prior to a certain date (e.g., present day) may be used. Various pre-prediction time periods may be utilized. For example the pre-prediction time period may include a one-month time period prior to the prediction time period, a three-month time period prior to the prediction time period, a six-month time period prior to the prediction time period, a one-year time period prior to the prediction time period, or another time period prior to the prediction time period.

In some embodiments, the determined adherence may be a binary value of yes or no reflecting whether the MPR is greater than or equal to a threshold. The threshold may be eighty percent, but other percentages such as approximately sixty percent, approximately sixty-five percent, approximately seventy percent, approximately seventy-five percent, approximately eighty percent, approximately eighty-five percent approximately ninety percent (e.g., ninety-one percent), or other percentages may be used. In some embodiments, the determined adherence may be a proportion of days covered.

In some embodiments, the adherence associated with the prescription drugs may be a subset of all available prescription drugs that may treat the condition. For example, 3, 4, 5, 6, 7, 8, 9, 10, 11, 12, 13, 14, or more than 14 prescription drugs may be selected and used when identifying potentially relevant adherence data. In some embodiments, 300, 400, 500, 600, 700, 800, 900, or 1000 prescription drugs may be selected and used. Other amounts of prescription drugs may be selected and used.

In an embodiment, the adherence determination module 406 may determine a pre-prediction time period medication possession ratio (MPR) of a Multiple Sclerosis drug associated with the Multiple Sclerosis treatment for the member to be determined. For example, the pre-prediction time period MPR of the Multiple Sclerosis drug may be determined based on prescription fills for the Multiple Sclerosis drug adjudicated by the PBM (including the number of days supply of the Multiple Sclerosis drug included in each prescription fill) over the pre-prediction time period. In some embodiments, the pre-prediction time period MPR includes the sum of days supplied during the pre-period divided by the length of the pre-period and adjusting for carry-over of available drug.

In an embodiment, the adherence determination module 406 may determine a pre-prediction time period gap of the Multiple Sclerosis drug for the member. The pre-prediction time period gap may include the number of days during the pre-prediction time period that the member is estimated to have been without the Multiple Sclerosis drug. For example, if on day one the member filled a prescription for a thirty-day supply of the Multiple Sclerosis drug (e.g., based on prescription claims adjudication data included within the member data 110), and the member did not refill the prescription until day thirty five, the adherence determination module 406 may determine a five day gap of the Multiple Sclerosis drug for the patient.

In an embodiment, the adherence determination module 406 may determine a pre-prediction time period compliance with the Multiple Sclerosis drug for the member. The pre-prediction time period compliance may include, for example, a cumulative number of days during the pre-prediction time period that the member is estimated to have been compliant with the Multiple Sclerosis drug. For example, the adherence determination module 406 may determine the pre-prediction time period compliance based on the number of days in the pre-prediction time period less the number of days gap of the Multiple Sclerosis drug for the member.

The prescription data determination module 408 may determine a number of anti-narcolepsy medications associated with the member. The determined number may be a number of fills that the member has had for the anti-narcolepsy medications during the pre-period. For example, based on the prescription data included within the member data 110, the prescription data determination module 408 may determine the number of prescription claims for anti-narcolepsy drugs adjudicated for the member during the pre-prediction time period.

In an embodiment, the demographics determination module 410 may determine a number of family members for the member based on the member data 110. In an embodiment, the demographics determination module 410 may determine consumer segmentation data (e.g., a NIELSEN PRIZM NE 66 segment code) associated with the member, e.g., based upon PRIZM NE 66 segment code criteria, which may classify the member based on geo-demographic information that may be included within the member data 110. In some embodiments, the number of family members may be the number of family members eligible for the prescription benefit in the household. In some embodiments, the number of family members may be the number of family members that have filled at least one of any prescription drugs during the pre-period.

In an embodiment, the adherence prediction module 412 may determine a likelihood that the member will be adherent to the Multiple Sclerosis treatment over a prediction time period based on the pre-prediction time period adherence data, member prescription data, member family data, and member demographic data. For example, in an embodiment the adherence prediction module 412 may determine the likelihood that the member will be adherent to the Multiple Sclerosis treatment over the next six month based on the determined pre-prediction time period fill-to-fill MPR, the determined pre-prediction period number of days gap in the Multiple Sclerosis treatment, the determined pre-prediction time period cumulative number of days compliant with the Multiple Sclerosis treatment, the number of anti-narcolepsy drugs associated with the member, the number of family members of the member, and/or the consumer segmentation data associated with the member. Additional factors, lesser factors, or alternate factors may be used in the determination.

In some embodiments, the Multiple Sclerosis treatment includes a drug treatment regimen. In some embodiments, the Multiple Sclerosis treatment may include a care plan.

The foregoing determination of adherence may be based on different weightings for the various examples. In an embodiment, a higher pre-prediction time period fill-to-fill MPR for the member may be indicative of a higher prediction time period adherence to the Multiple Sclerosis treatment. In an embodiment, a higher number of pre-prediction period gaps in the Multiple Sclerosis treatment may be indicative of a lower prediction time period adherence to the Multiple Sclerosis treatment. In an embodiment, a higher number of pre-prediction time period cumulative days compliant to the Multiple Sclerosis treatment may be indicative of a higher prediction time period adherence to the Multiple Sclerosis treatment. In an embodiment, a higher number of family members of the member may be indicative of a lower prediction time period adherence to the Multiple Sclerosis treatment. In an embodiment, a higher number of anti-narcolepsy drugs associated with the member may be indicative of a higher prediction time period adherence to the Multiple Sclerosis treatment. In an embodiment a particular consumer segment (e.g., a PRIZM NE 66 segment code 47) associated with the member may be indicative of a higher prediction time period adherence to the Multiple Sclerosis treatment, and a particular consumer segment (e.g., a PRIZM NE 66 segment code 16) may be indicative of a lower prediction time period adherence to the Multiple Sclerosis treatment.

The above factors are example factors that may be used with the predictive model. However, more or less factors, and/or different factors, may be identified and used with the predictive model. The factors may depend on the data analysis performed, the model built, In some embodiments, the adherence prediction module 412 predicts the probability that a member will achieve an MPR>=80%. In some embodiments, the adherence prediction module 412 predicts the probability that a member will achieve a sufficiently high Proportion of Days Covered (PDC). In some embodiments, the adherence prediction module 412 predicts the probability that the member will stop their therapy altogether. Other types of adherences predictions made by made by the adherence prediction module 412 for Multiple Sclerosis treatment or other types of treatments.

The intervention module 414 determines an intervention based on the likelihood that the member will be adherent to the Multiple Sclerosis treatment over the prediction time period. In some embodiments, the intervention may include a member consultation. In some embodiments, the intervention includes assistance in transitioning fills of a maintenance prescription drug from a retail pharmacy to a mail order pharmacy or other drug distribution facility (e.g., for prescription drugs associated with the Multiple Sclerosis treatment). In some embodiments, the intervention includes offering or providing a subsidy for the Multiple Sclerosis treatment. In some embodiments, the intervention includes enrollment in care program (e.g., a nursing involvement program such as MS CARELOGIC program by Express Scripts Holding Company). In some embodiments, the intervention includes delivery of adherence devices such as a dose reminder.

In some embodiments, the adherence prediction module 410 may be used in underwriting decisions for health insurance. In some embodiments, the adherence prediction module 410 may be used to communicate with a prescriber or other health care professional to counsel the member on the importance of adherence.

In some embodiments, a likelihood of non-adherence may be determined by the adherence prediction module 412 and an intervention may be made on the basis of the likelihood of non-adherence by the intervention module 414.

Figure 5:
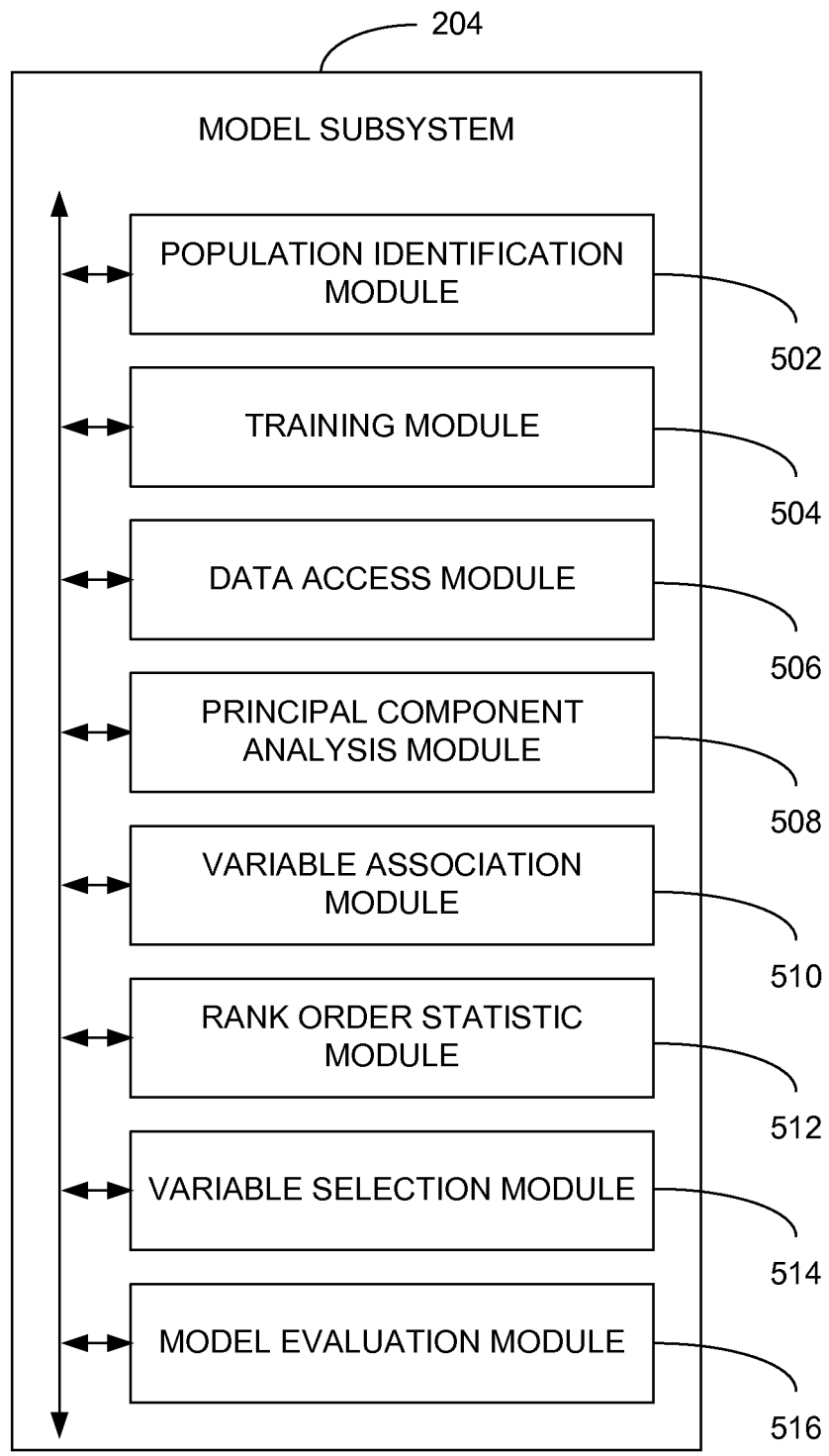
FIG. 5 is a block diagram of an example model subsystem that may be deployed within the user device of FIG. 2 or the benefit manager device of FIG. 3, according to an example embodiment.

FIG. 5 illustrates an example of the model subsystem 204 that may be deployed in the user device 102, the benefit manager device 106, or otherwise deployed in another system. One or more modules are communicatively coupled and included in the model subsystem 204 to enable a predictive model to be generated for predicting a likelihood of member adherence to a treatment over a prediction time period. In one embodiment, the model subsystem 204 may enable a model to be generated for predicting a likelihood of member adherence to a Multiple Sclerosis treatment over a prediction time period. In other embodiments, the model subsystem 204 may enable a model to be generated for predicting a likelihood of member adherence to other treatments over a prediction time period. The modules of the model subsystem 204 that may be included are a population identification module 502, a training module 504, a data access module 506, a principal component analysis module 508, a variable association module 510, a rank order statistic module 512, a variable selection module 514, and a model evaluation module 516.

In some embodiments, the modules of the model subsystem 204 may be distributed so that some of the modules are deployed in the user device 102 and some modules are deployed in the benefit manager device 106. In one embodiment, the modules are deployed in memory and executed by a processor coupled to the memory. The functionality contained within the modules 502-516 may be combined into a lesser number of modules, further divided among a greater number of modules, or redistributed among existing modules. Other configurations including the functionality of the modules 502-516 may be used.

The population identification module 502 may identify a population for generating a predictive model. In an embodiment, the population identification module 502 may access the member data 110, and may query the member data 110 to identify members undergoing a Multiple Sclerosis treatment. For example, the population identification module 502 may query claims adjudication data relative to one, or more than one, Multiple Sclerosis drugs, and may identify the members filling the prescriptions for the Multiple Sclerosis drugs. The members identified as filling prescriptions for the Multiple Sclerosis drugs may make up a modeling population. In some embodiments, a subset of the identified members may identified based on one, or more than one, additional attributes. For example, only the members of a client, or a set of clients of a benefit manager, may be identified by the population identification module 502.

In some embodiments, the population identification module 502 may access the member data 110 from the database 108. In some embodiments, accessing the member data 110 from the database 110 may include receiving the member data 110 over the network 104 from the user device 102, from the benefit manager device 106, or from a different device.

The training module 504 may identify a subset of the modeling population. The subset of the modeling population may be a training population that may be utilized for generating the predictive model. In an embodiment, the training module 504 may randomly select the training population from the modeling population. In some embodiments, the size of the training population selected by the training module 504 may vary depending upon the size of the modeling population. For example, the training population may include approximately 50% of the modeling population. In other embodiments, the training population may include different percentages of the modeling population, such as 40% of the modeling population, 30% of the modeling population, 20% of the modeling population, 10% of the modeling population, or another desired percentage of the modeling population.

The data access module 506 may access the member data 110 associated with the members included in the training population. The data access module 506 may identify variables or measurable attributes associated with the members and values for the variables associated with the members based on the member data 110. In an embodiment, variables may include types of medications associated with each member, MPR for each medication associated with each member, compliance associated with each medication associated with each member, demographic attributes associated with each member, medical conditions associated with each member, and the like. In some embodiments, the data access module 506 may calculate values associated with one or more variables based on the member data 110. For example, the MPR for a prescription associated with a member may be calculated based on fill and/or refill dates associated with the prescription, the dosage information associated with the prescription, and the quantity of medication associated with the prescription. Values for various additional and/or alternative variables may be calculated based on the member data 110.

In some embodiments, the data access module 506 may access the member data 110 from the database 108. In some embodiments, accessing the member data 110 from the database 108 may include receiving the member data 110 over the network 104 from the user device 102, from the benefit manager device 106, or from a different device.

The principal component analysis module 508 may perform principal component analysis for continuous variables identified by the data access module 506, in a manner known in the art. In an embodiment, the principal component analysis module 508 may apply principal component analysis on the data correlation matrix. In an embodiment, the principal component analysis module 508 may identify one or more than one principal components having an eigenvalue equal to, or greater than, about one. In an embodiment, the identified principal components may include a linear combination of all of the variables identified by the data access module.

The variable association module 510 may associate at least a portion of the variables identified by the data access module 506 with one of the principal components identified by the principal component analysis module 508. The variables identified by the data access module 506 may be associated with a principal component based on the variable loading value associated with each variable. The variable association module 510 may associated the variables with the identified principal component on which the variable has the highest loading.

In an embodiment, the variable association module 510 may select variables for potential use in the predictive model based on a statistical significance of the variable to the target variable (i.e., the variable being predicted by the model, such as adherence). In an embodiment, the variable association module 510 may select variables for potential use in the predictive model based on an independent binary logistic regression model run against each continuous variable on each of the principal components using a backwards selection technique. Based on the independent binary logistic regression model, variables not identified as being statistically significant may be excluded from the predictive model.

The rank order statistic module 512 may determine which variables selected for potential use in the predictive model provide the greatest contribution to the rank order statistic (e.g., the c-statistic) relative to the target variable. In an embodiment, the rank order statistic module 512 may utilize a stepwise selection procedure to determine the variables that provide the greatest contribution to the rank order statistic. In an embodiment, a logistic regression model may be run against each of the variables selected for potential use in the predictive model, and the c-statistic for each variable may be calculated. The variables may be rank ordered according to the calculated c-statistic associated with each of the variables.

The rank order statistic module 512 may select one, or more than one, of the rank ordered variables based on a relative improvement of the c-statistic provided by the one, or more than one rank ordered variables. For example, the improvement of the c-statistic (i.e., the incremental increase in the c-statistic from one rank to the next successive rank in the rank ordered variables) may decrease and/or flatten out at a point of increasing rank. In an embodiment, the one, or more than one variables prior to the decreased improvement in the c-statistic may be selected as a potential input variable for further use in the predictive model.

The variable selection module 514 may select the final variables for use in the predictive model. In an embodiment, the variable selection module 514 may bin each potential input variable. In an embodiment, the bin intervals may be selected such that each bin may have between about 5% to about 10%, or greater, of the total counts (i.e., of the total number members for which values of the variable are included). The probability, p, of a positive target variable (e.g., the probability of compliance with the Multiple Sclerosis treatment) for each bin is calculated based on the number of adherent members (e.g., members having a fill-to-fill MPR of a drug included within the Multiple Sclerosis treatment above a threshold value, such as 91, or other suitable value considered to be indicative of adherence) in the bin population. The variable selection module 514 may further calculate a log it value for each bin as log $(p/(1-p))$. As necessary, the variable selection module 514 may adjust the bins to ensure that there is a pattern in the log it (e.g., an increasing, decreasing, or quadratic pattern). The variable selection module 514 may further regress the log its against the bins to estimate the signal. In an embodiment, the variable selection module may replace the variables with the corresponding transformed log its in the predictive model. In an embodiment, binary variables may be not be binned.

In an embodiment, the variable selection module 514 may run the logistic regression against the transformed variables to determine whether the transformed variables are statistically significant for predicting the target variable, e.g., base on the variables providing a statistically significant contribution to the c-statistic. If a transformed variable is statistically significant to the overall model, the variable may be accepted for the predictive model. If the variable is not statistically significant, the variable may be removed from the model. In some embodiments, if a variable is removed from the model, the next variable in the rank ordered variables may be selected as a possible substitute variable for inclusion in the model. A selected possible substitute variable may be binned, and the log its for the substitute variable may be determined, as described above. Further, the variable selection module 514 may run the logistic regression against the transformed substitute variable to determine if the variable is statistically significant.

The model evaluation module 516 may evaluate the performance of the generated predictive model. In an embodiment, estimates provided by the predictive model may not be directly interpretable, e.g., due to the use of log its as the predictor variables in the predictive model. In some embodiments, the model evaluation module 516 may determine a percent contribution of each variable based on the absolute value of the estimate for a variable divided by the sum of the absolute values for the estimates for all of the variables.

In some embodiments, the model evaluation module 516 may evaluate the performance of the generated predictive model utilizing a subset of the population identified by the population identification module 502. In some embodiments, the model evaluation module 515 may evaluate the performance of the predictive model utilizing the members not selected as the training population. For example, the model evaluation module 516 may determine a likelihood of adherence of one, or more than one, members not included within the training population based on the predictive model. In some embodiments the model evaluation module 516 may determine whether the one or more members not included within the training population were adherent to the Multiple Sclerosis treatment (e.g., by determining an MPR for the member, or members, based on the member data 110). The model evaluation module 516 may compare the likelihood of adherence predicted by the predictive model to the actual adherence determined for the one or more members.

Figure 6:
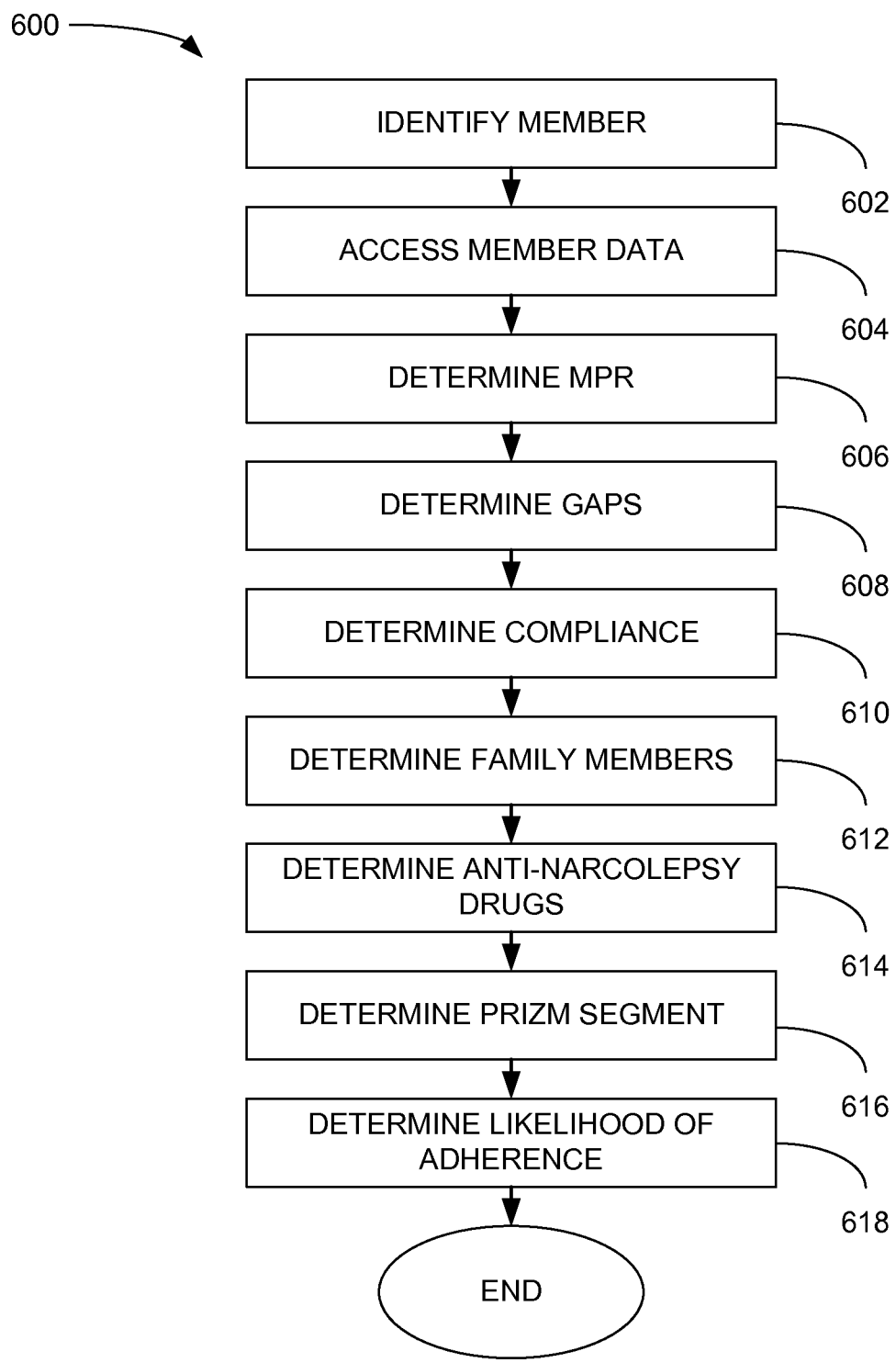
FIG. 6 is a process flow illustrating a method for predicting a likelihood of adherence to a multiple Sclerosis treatment, according to an example embodiment.

FIG. 6 illustrates a method 600 for determining a likelihood that a member will be adherent to a Multiple Sclerosis treatment during a prediction time period, according to an example embodiment. The method 600 may be performed by the user device 102, by the benefit manager device 106, partially by the user device 102 and partially be the benefit manager device 106, or may be otherwise performed.

A member undergoing a Multiple Sclerosis treatment is identified at block 602. In an embodiment, the member undergoing the Multiple Sclerosis treatment may be identified based on a pharmacy prescription claim for a Multiple Sclerosis drug submitted by a pharmacy for adjudication by the PBM. For example, when the member attempts to fill (e.g., initially and/or as a refill) a prescription for a Multiple Sclerosis drug, the pharmacy may submit a claim for adjudication by the PBM administering a drug benefit program under which the member may receive coverage for prescription drugs. The member undergoing the Multiple Sclerosis treatment may be identified based on the submitted claim. In an embodiment, the member undergoing the Multiple Sclerosis treatment may be identified based on a query of claims for Multiple Sclerosis drugs adjudicated by the PBM. The member undergoing the Multiple Sclerosis treatment may be otherwise identified.

Member data associated with the member undergoing the Multiple Sclerosis treatment may be identified at block 604. The member data 110 may include pre-prediction period adherence data associated with the member, member prescription data associated with the member, member family data associated with the member, and member demographic data. Accessing the member data 110 may include accessing the member data 110 from the database 108 and/or receiving the member data 110 from the database 108, via network 104, or otherwise receiving the member data.

The MPR for a Multiple Sclerosis drug associated with the member may be determined at block 606. The MPR for the member may be determined based on the member data 110 accessed at block 604. For example, the member data may include claims adjudication data, which may indicate what prescriptions for Multiple Sclerosis drugs were filled by the member, when the prescriptions were filled, the quantity and dosage of the prescription, and the like. Based on the claims adjudication data the MPR for the member may be determined. In an embodiment, the determined MPR may be a fill-to-fill MPR, that is the MPR may be determined from fill date to fill date of the prescription.

The number of gaps, measured in days, in the Multiple Sclerosis treatment of the member for a pre-prediction time period may be determined at block 608. The pre-prediction time period may include a period of time prior to the time period for which the likelihood of adherence is being determined. The number of gaps in the Multiple Sclerosis treatment may be determined based on the member data 110. For example, claims adjudication data may indicate that a prescription for a thirty day supply of a Multiple Sclerosis drug was filled, but that the prescription for the Multiple Sclerosis drug was not refilled until thirty three days later, indicating that the member had a three day gap in the Multiple Sclerosis treatment.

In a related manner, the number of days during the pre-prediction time period during which the member was compliant with the Multiple Sclerosis treatment may be determined at block 610. The number of days during the pre-prediction time period during which the member was compliant may be determined based on the member data 110. For example, the member may be considered to be compliant with the Multiple Sclerosis treatment if the member is determined to be in possession of a sufficient quantity of medication required by the Multiple Sclerosis treatment, e.g., based on claims adjudication data indicating that the member has refilled prescriptions associated with the Multiple Sclerosis treatment in a timely manner, before exhausting the previous fill of the prescription.

A number of family members of the member may be determined at block 612. The number of family members of the member may be determined based on the member data, for example based on a number of individuals covered by a drug benefit plan associated with the member.

A number of anti-narcolepsy drugs associated with the member may be determined at block 614. For example, in an embodiment, the number of anti-narcolepsy drugs associated with the member may be determined based on claims adjudication data that indicate prescriptions filled by the member for anti-narcolepsy drugs.

Consumer segment data for the member may be determined at block 616, based on the member data. The member data may include demographic information associated with the member. Consumer segment data for the member may be determined based on the various relevant criteria associated with the member.

A likelihood of adherence to the Multiple Sclerosis treatment during the prediction time period may be determined for the member at block 618. The likelihood of adherence to the Multiple Sclerosis treatment during the prediction time period may be determined based on the determined pre-prediction time period fill-to-fill MPR, the determined pre-prediction period number of days gap in the Multiple Sclerosis treatment, the determined pre-prediction time period cumulative number of days compliant with the Multiple Sclerosis treatment, the number of anti-narcolepsy drugs associated with the member, the number of family members of the member, and the consumer segment data PRIZM NE 66 segment code associated with the member.

Figure 7:
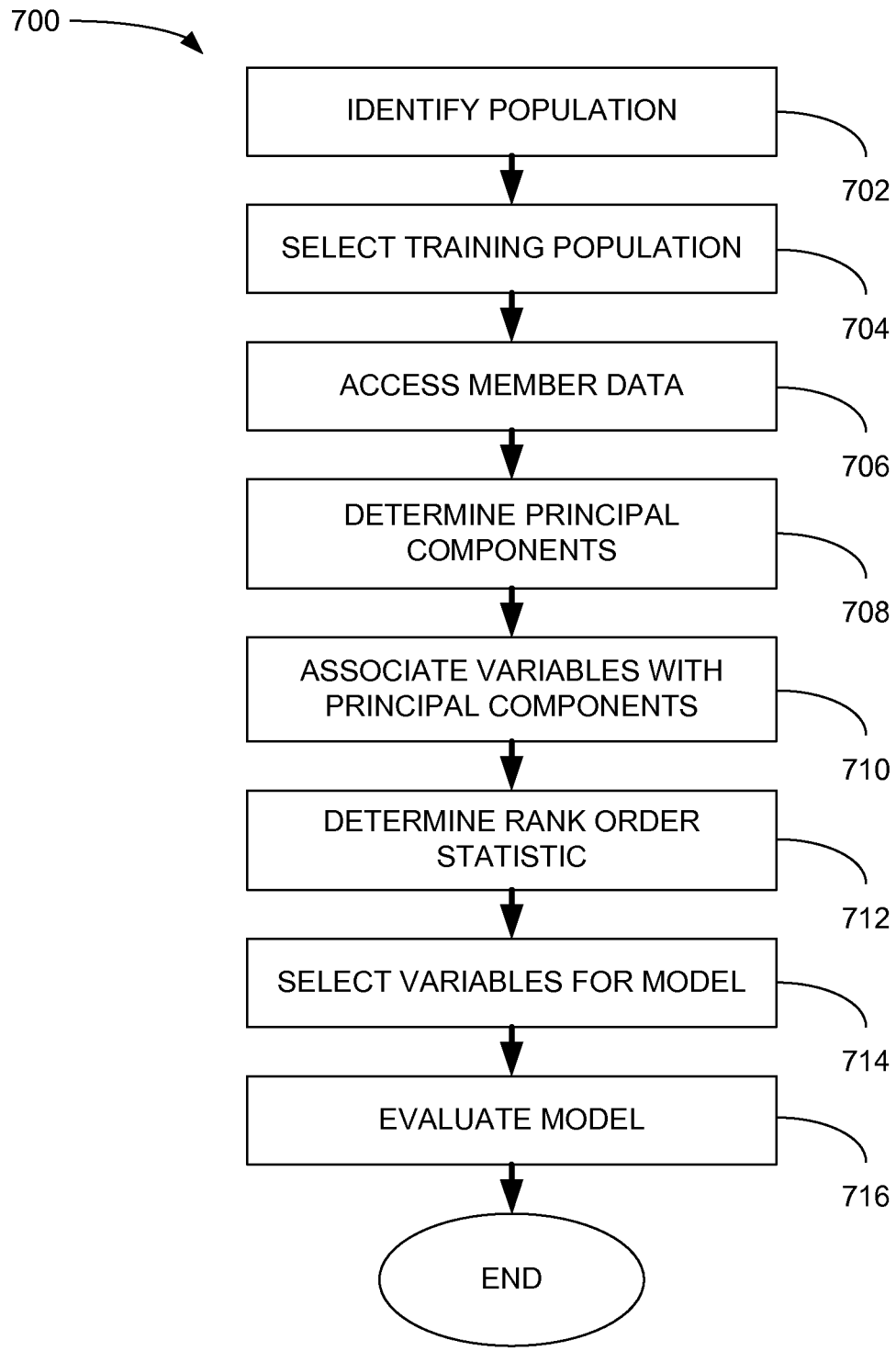
FIG. 7 is a process flow illustrating a method of generating a predictive model, according to an example embodiment.

FIG. 7 illustrates a method 700 for generating a predictive model, according to an example embodiment. The method 700 may be performed by the user device 102, by the benefit manager device 106, partially by the user device 102 and partially be the benefit manager device 106, or may be otherwise performed.

A population for generating the predictive model may be identified at block 702. In an embodiment in which the predictive model may predict a likelihood of adherence to a Multiple Sclerosis treatment, identifying the population for generating the predictive model may include identifying one, or more than one, members undergoing a Multiple Sclerosis treatment. For example, identifying the population may include querying the user data relative to one, or more than one, treatments and/or drugs associated with a Multiple Sclerosis treatment. For example, claims adjudication data, which may be included in the member data 110, may be queried relative to one, or more than one, drugs associated with a Multiple Sclerosis treatment. Based on claims adjudication data for drugs associated with a Multiple Sclerosis treatment, members filling prescriptions for the drugs associated with a Multiple Sclerosis treatment may be identified.

A training population may be selected at block 704. For example, a subset of the identified population of members undergoing a Multiple Sclerosis treatment may be identified and selected as a training population for generating the predictive model. In an embodiment, the training population may include a randomly selected subset of the identified population of members undergoing a Multiple Sclerosis treatment. Additionally and/or alternatively, the training population may include a subset of the identified population of members undergoing a Multiple Sclerosis treatment that may be selected based on one or more criterion. The size of the identified training population may vary, e.g., depending upon the size of the identified population of members undergoing a Multiple Sclerosis treatment. For example, the training population may include between about 50% to about 10% of the identified population of members undergoing a Multiple Sclerosis treatment.

Member data associated with the training population may be accessed at block 706. The member data 110 may include information regarding prescriptions that have been filled by the members included in the training population (e.g., including identification of prescribed drugs, dates that prescriptions were filled, duration of treatment, disease state and/or ailment being treated by the prescriptions, and the like), demographic data (e.g., including gender, ethnicity, age, geographic location, family size, and the like), as well as various additional and/or alternative information. Accessing the member data 110 may include identifying variables associated with the members included in the training population. In some embodiments, additional variables may be determined based upon the member data 110. For example, an MPR for a prescription drug may be determined based one, for example, fill dates and refill dates for a prescription and a quantity of medication included in a fill of the prescription. Various additional and/or alternative variables may also be determined based on the member data 110.

Accessing the member data 110 may include accessing the member data from the database 108, and/or receiving the member data 110 from the database 108, directly, via network 104, or otherwise receiving the member data.

Principal components may be determined at block 708 based on one or more than one variables identified based on the accessed member data. In some embodiments, principal components may be identified applying principal component analysis to the data correlation matrix. In an embodiment, principal components may be determined based components having an eigenvalue equal to, or greater than, about one. In an embodiment, the principal components may include a linear combination of all of the variables identified by accessing the member data.

At least a portion of the variables may each be associated with a respective principal component at block 710. In an embodiment, the variables may be a associated with a principal component based on the variable loading value associated with each variable. The variables may each be associated with the principal component on which the variable has the highest loading.

In some embodiments, associating variables with principal components may include determining a statistical significance of one or more than one of the variables to the target variable. In an embodiment, the statistical significance of the variables to the target variable may include running an independent binary logistic regression model against each continuous variable on each of the principal components using a backwards selection technique. In some embodiments, variables that are not statistically significant to the target variable may be excluded.

A rank order statistic may be determined at block 712 for the variables determined to be statistically significant to the target variable. In an embodiment, determining the rank order statistic (c-statistic) for the variables may include utilizing a stepwise selection procedure to determine the variables that provide the greatest contribution to the rank or statistic. In an embodiment, a logistic regression model may be run against each of the variables determined be statistically significant to the target variable, and the c-statistic for each variable may be calculated. The variables may be ranked ordered according to the calculated c-statistic associated with each of the variables.

In an embodiment, one, or more than one, of the rank ordered variables may be selected based on a relative improvement of the c-statistic provided by the one, or more than on, rank ordered variables. In an embodiment, the variables providing the greatest improvement to the c-statistic may be selected as a potential input variable for use in the predictive model.

Final variables for use in the predictive model may be selected at block 714 from among the potential input variables. In an embodiment, each of the potential input variables may be binned, with bin intervals for each potential input variable being selected to have between about 5% to about 10%, or greater, of the total counts in each bin. A log it may be calculated for each bin as $\log(p/(1-p))$, in which p is the probability of a positive target variable in each bin. In some embodiments, the bin intervals may be adjusted to provide a pattern in the log it (e.g., an increasing, decreasing, or quadratic pattern). The log its may be regressed against the bins to estimate the signal. In some embodiments, the transformed log its may replace the variables in the predictive model.

In an embodiment, a logistic regression may be run against each of the transformed variable to determine whether the transformed variables are statistically significant for predicting the target variable, e.g., based on the variables providing a statistically significant contribution to the c-statistic. If a transformed variable is not statistically significant to the target variable, in some embodiments, the variable may be discarded. In some embodiments, if a variable is discarded, another potential input variable may be selected, such as the next most significant rank ordered variable.

The predictive model may be evaluated at block 716. In an embodiment, the predictive model may be evaluated using at least a portion of the identified population of members not selected as the training population. In an embodiment, evaluating the predictive model may include utilizing the predictive model to predict a likelihood of adherence to a Multiple Sclerosis treatment for multiple members, and comparing the predicted likelihood to a determined adherence for the members (e.g., based on calculated MPR for the members).

Figure 8:
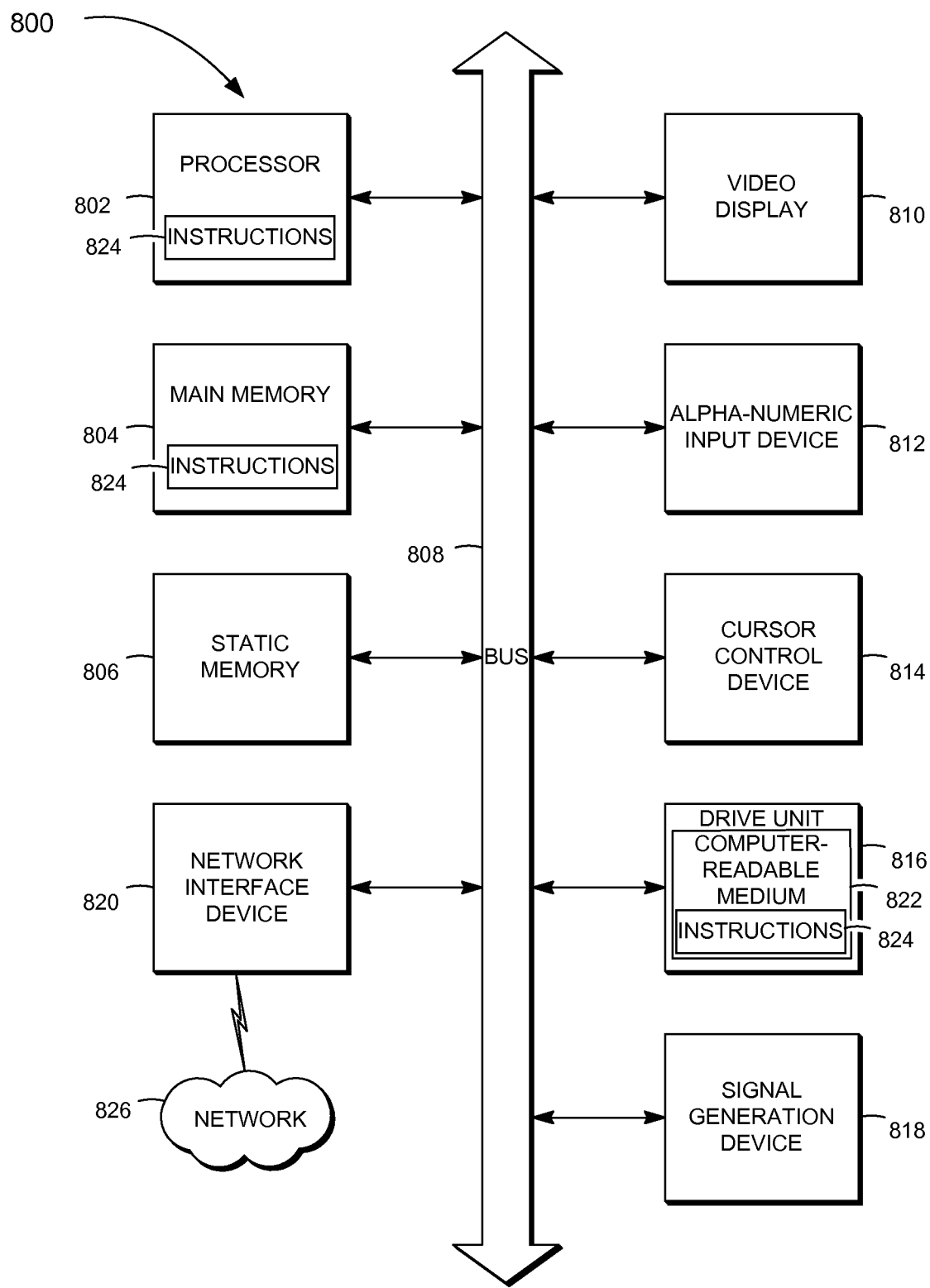
FIG. 8 is a block diagram of a machine in the example form of a computer system within which a set of instructions for causing the machine to perform any one or more of the methodologies discussed herein may be executed or stored.

FIG. 8 shows a block diagram of a machine in the example form of a computer system 800 within which a set of instructions may be executed causing the machine to perform any one or more of the methods, processes, operations, or methodologies discussed herein. The user device 102, and/or the benefit management device 106 may include the functionality of the one or more computer systems 800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 800 includes a processor 802 (e.g., a central processing unit (CPU) a graphics processing unit (GPU) or both), a main memory 804 and a static memory 806, which communicate with each other via a bus 808. The computer system 800 further includes a video display unit 810 (e.g., a liquid crystal display (LCD) or a cathode ray tube (CRT)). The computer system 800 also includes an alphanumeric input device 812 (e.g., a keyboard), a cursor control device 814 (e.g., a mouse), a drive unit 816, a signal generation device 818 (e.g., a speaker) and a network interface device 820.

The drive unit 816 includes a computer-readable medium 822 on which is stored one or more sets of instructions (e.g., software 824) embodying any one or more of the methodologies or functions described herein. The software 824 may also reside, completely or at least partially, within the main memory 804 and/or within the processor 802 during execution thereof by the computer system 800, the main memory 804 and the processor 802 also constituting computer-readable media.

The software 824 may further be transmitted or received over a network 826 via the network interface device 820.

While the computer-readable medium 822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a member undergoing a Multiple Sclerosis treatment is identified. Member data associated with the member undergoing the Multiple Sclerosis treatment is accessed. Pre-prediction time period adherence data associated with the member, member prescription data associated with the member, member family data associated with the member, and member demographic data associated with the member are determined based on the member data associated with the member. A likelihood that the member will be adherent to the Multiple Sclerosis treatment over a prediction time period is determined based on the pre-prediction time period adherence data, member prescription data, member family data, and member demographic data.

In an example embodiment, a population of members undergoing a Multiple Sclerosis treatment is identified. A training population including a subset of the members undergoing the Multiple Sclerosis treatment is identified. Member data for the training population is accessed. The member data includes adherence data, prescription data, and demographic data associated with the subset of the members undergoing the Multiple Sclerosis treatment. One or more principal components are determined from a plurality of variables included within the member data, the one or more principal components having an Eigen value greater than or equal to about 1. Each of the plurality of variables are associated with one of the one or more principal components based on a statistical significance between each of the plurality of variables an the one or more principal components. A rank order statistic associated with the plurality of variables relative to adherence to the Multiple Sclerosis treatment is determined. A modeling subset of the plurality of variables is selected based on the rank order statistic associated with each of the plurality of variables. The selected modeling subset is evaluated for statistical significance to adherence to the Multiple Sclerosis treatment.

Thus, methods and systems for predicting adherence to Multiple Sclerosis treatment have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving, on a processor of a benefit manager server, a plurality of claims from at least one pharmacy device over the Internet;
identifying, on the processor of the benefit manager server, a population of members undergoing a Multiple Sclerosis treatment based on claims data received from the at least one pharmacy device over the Internet;
selecting, on the processor of the benefit manager server, a training population including a subset of the members undergoing the Multiple Sclerosis treatment;
transmitting a request from the benefit manager server to a database over the Internet for member data associated with the subset of the members undergoing Multiple Sclerosis treatment;
receiving, on the processor of the benefit manager server, member data for the training population, the member data including adherence data, prescription data, and demographic data associated with the subset of the members undergoing the Multiple Sclerosis treatment from the database over the Internet;
generating, on the processor of the benefit manager server, a predictive model comprising a plurality of variables;
determining, on the processor of the benefit manager server, one or more principal components from the plurality of variables included within the member data, the one or more principal components having an eigen-value greater than or equal to about 1;
associating, on the processor of the benefit manager server, each of the plurality of variables with one of the one or more principal components based on a statistical significance between each of the plurality of variables and the one or more principal components;

determining, on the processor of the benefit manager server, a rank order statistic associated with the plurality of variables relative to adherence to the Multiple Sclerosis treatment;

discarding, on the processor of the benefit manager server, one or more of the plurality of variables found to be statistically insignificant to a target variable based on the one or more principal components and the rank order statistic;

selecting, on the processor of the benefit manager server, a modeling subset of the plurality of variables based on the rank order statistic associated with each of the plurality of variables, the modeling subset excluding any discarded variables;

adjusting, on the processor of the benefit manager server, the predictive model such that the predictive model only includes variables included in the modeling subset; and evaluating, on the processor of the benefit manager server, the predictive model for statistical significance to adherence to the Multiple Sclerosis treatment, wherein the population of members undergoing Multiple Sclerosis treatment comprises more than one thousand members.

2. The method of claim 1, further comprising:
validating the selected modeling subset using a validation population including a second subset of the members undergoing the Multiple Sclerosis treatment.

3. The method of claim 1, wherein associating each of the plurality of variables with one or the one or more principal components comprises:
determining a loading value associated with each of the plurality of variable and with each of the one or more principal components; and
associating each of the plurality of variables with the principal component on which each variable has the highest loading value.

4. The method of claim 1, wherein associating each of the plurality of variable with one of the one or more principal components further comprises:
determining the statistical significance between each of the plurality of variables and the one or more principal components including running an independent binary logistic regression model against each of the plurality of variables associated with one of the one or more principal components using a backwards selection; and
selecting one or more of the plurality of variables based on the independent binary regression.

5. The method of claim 1, wherein selecting the modeling subset of the plurality of variables comprises:
selecting one or more of the plurality of variables providing a greatest relative improvement to the rank order statistic.

6. The method of claim 1, further comprising:
binning each of the modeling subset of the plurality of variables;
calculating a probability of adherence for each bin; and
calculating a log it value for each bin based on the probability of adherence for each bin.

7. The method of claim 6, wherein binning each of the modeling subset of the plurality of variables comprises:
selecting a bin interval for each of the modeling subset of the plurality of variables to include greater than, or equal to, about 5% of the training population.

8. The method of claim 7, further comprising:
adjusting the bin interval for at least one of the modeling subset of the plurality of variables to provide a pattern of the log it value for the at least one of the modeling subset of the plurality of variables.

9. The method of claim 1, wherein evaluating the selected modeling subset for statistical significance to adherence to the Multiple Sclerosis treatment comprises:
determining a contribution of each of the selecting modeling subset to the c-statistic.

10. A method comprising:
receiving, on a benefit manager device having an adherence subsystem and a model subsystem, a plurality of claims from at least one pharmacy device over the Internet;

identifying, on a population identification module of the model subsystem, a population of members undergoing a Multiple Sclerosis treatment for generating a predictive model based on claims data received from the at least one pharmacy device over the Internet;

selecting, on a training module of the model subsystem, a training population including a subset of the members undergoing the Multiple Sclerosis treatment;

transmitting a request from the benefit manager server to a database over the Internet for member data associated with the subset of the members undergoing Multiple Sclerosis treatment;

accessing, on a data access module of the model subsystem, member data for the training population, the member data including adherence data, prescription data, and demographic data associated with the subset of the members undergoing the Multiple Sclerosis treatment from the database over the Internet;

generating, on the data access module of the model subsystem, a predictive model comprising a plurality of variables;

determining, on a principal component analysis module of the model subsystem, one or more principal components from the plurality of variables included within the member data, the one or more principal components having an eigenvalue greater than or equal to about 1;

associating, on a variable association module of the model subsystem, each of the plurality of variables with one of the one or more principal components based on a statistical significance between each of the plurality of variables and the one or more principal components;

determining, on a rank order statistic module of the model subsystem, a rank order statistic associated with the plurality of variables relative to adherence to the Multiple Sclerosis treatment;

discarding, on a variable selection module of the model subsystem, one or more of the plurality of variables found to be statistically insignificant to a target variable based on the one or more principal components and the rank order statistic;

selecting, on the variable selection module of the model subsystem, a modeling subset of the plurality of variables based on the rank order statistic associated with each of the plurality of variables for using in the predictive model, the modeling subset excluding any discarded variables;

binning, on the variable selection module, each of the modeling subset of the plurality of variables;

determining, on the variable selection module, a probability of adherence for each bin by calculating a probability of compliance with the multiple Sclerosis treatment;

determining, on a model evaluation module of the model subsystem, statistical significance to adherence to the Multiple Sclerosis treatment for the selected modeling subset; and adjusting, on the model evaluation module, the predictive model such that the predictive model only includes variables included in the modeling subset, wherein the population of members undergoing Multiple Sclerosis treatment comprises more than one thousand members.

\* \* \* \* \*